United States Patent
Doering

(10) Patent No.: US 10,959,929 B2
(45) Date of Patent: Mar. 30, 2021

(54) DEODORANTS WITH PROLONGED SCENT ADHESION

(71) Applicant: Henkel AG & Co. KGaA, Duesseldorf (DE)

(72) Inventor: Thomas Doering, Dormagen (DE)

(73) Assignee: Henkel AG & Co. KGaA, Duesseldorf (DE)

(*) Notice: Subject to any disclaimer, the term of this patent is extended or adjusted under 35 U.S.C. 154(b) by 5 days.

(21) Appl. No.: 16/151,545

(22) Filed: Oct. 4, 2018

(65) Prior Publication Data

US 2019/0105251 A1 Apr. 11, 2019

(30) Foreign Application Priority Data

Oct. 5, 2017 (DE) .................. 10 2017 217 735.7

(51) Int. Cl.
| | |
|---|---|
| A61K 8/37 | (2006.01) |
| A61K 8/31 | (2006.01) |
| A61K 8/33 | (2006.01) |
| A61K 8/34 | (2006.01) |
| A61K 8/35 | (2006.01) |
| A61Q 15/00 | (2006.01) |

(52) U.S. Cl.
CPC ............. *A61K 8/375* (2013.01); *A61K 8/31* (2013.01); *A61K 8/33* (2013.01); *A61K 8/34* (2013.01); *A61K 8/347* (2013.01); *A61K 8/35* (2013.01); *A61K 8/37* (2013.01); *A61Q 15/00* (2013.01); *A61K 2800/30* (2013.01)

(58) Field of Classification Search
CPC . A61K 8/375; A61K 8/31; A61K 8/33; A61K 8/34; A61K 8/347; A61K 8/35; A61K 8/37; A61K 2800/30; A61K 2800/5922; A61K 2300/00; A61Q 15/00; A61Q 13/00
See application file for complete search history.

(56) References Cited

U.S. PATENT DOCUMENTS

| | | | |
|---|---|---|---|
| 2014/0121174 A1* | 5/2014 | von Aspern | A61Q 5/006 514/25 |
| 2014/0255077 A1* | 9/2014 | Mobarak | A61K 8/9789 401/88 |
| 2014/0274870 A1* | 9/2014 | Cetti | A61K 8/362 512/2 |

(Continued)

FOREIGN PATENT DOCUMENTS

| | | |
|---|---|---|
| DE | 102015210481 A1 | 12/2016 |
| DE | 102015225958 A1 | 6/2017 |
| DE | 102016221155 A1 | 5/2018 |

(Continued)

OTHER PUBLICATIONS

Mintel: "48H Deospray", Rossmann Isana Men Fresh Deodorants; http://www.gnpd.com.

*Primary Examiner* — Robert A Wax
*Assistant Examiner* — Quanglong N Truong
(74) *Attorney, Agent, or Firm* — Lorenz & Kopf, LLP

(57) ABSTRACT

The present disclosure relates to cosmetic agents which, in addition to ethanol and fragrances, contain at least one fixing agent mixture for the fragrances and have a high and long-lasting deodorizing action. Furthermore, the present disclosure relates to the use of these agents for the treatment of body odor.

18 Claims, 1 Drawing Sheet

(56) References Cited

U.S. PATENT DOCUMENTS

2015/0313820 A1* 11/2015 Kulke .................. A61K 8/4986
                                                        424/48
2018/0140522 A1    5/2018 Doering et al.

FOREIGN PATENT DOCUMENTS

| GB | 2558979 A    | 7/2018  |
|----|--------------|---------|
| WO | 2016205301 A1 | 12/2016 |

* cited by examiner

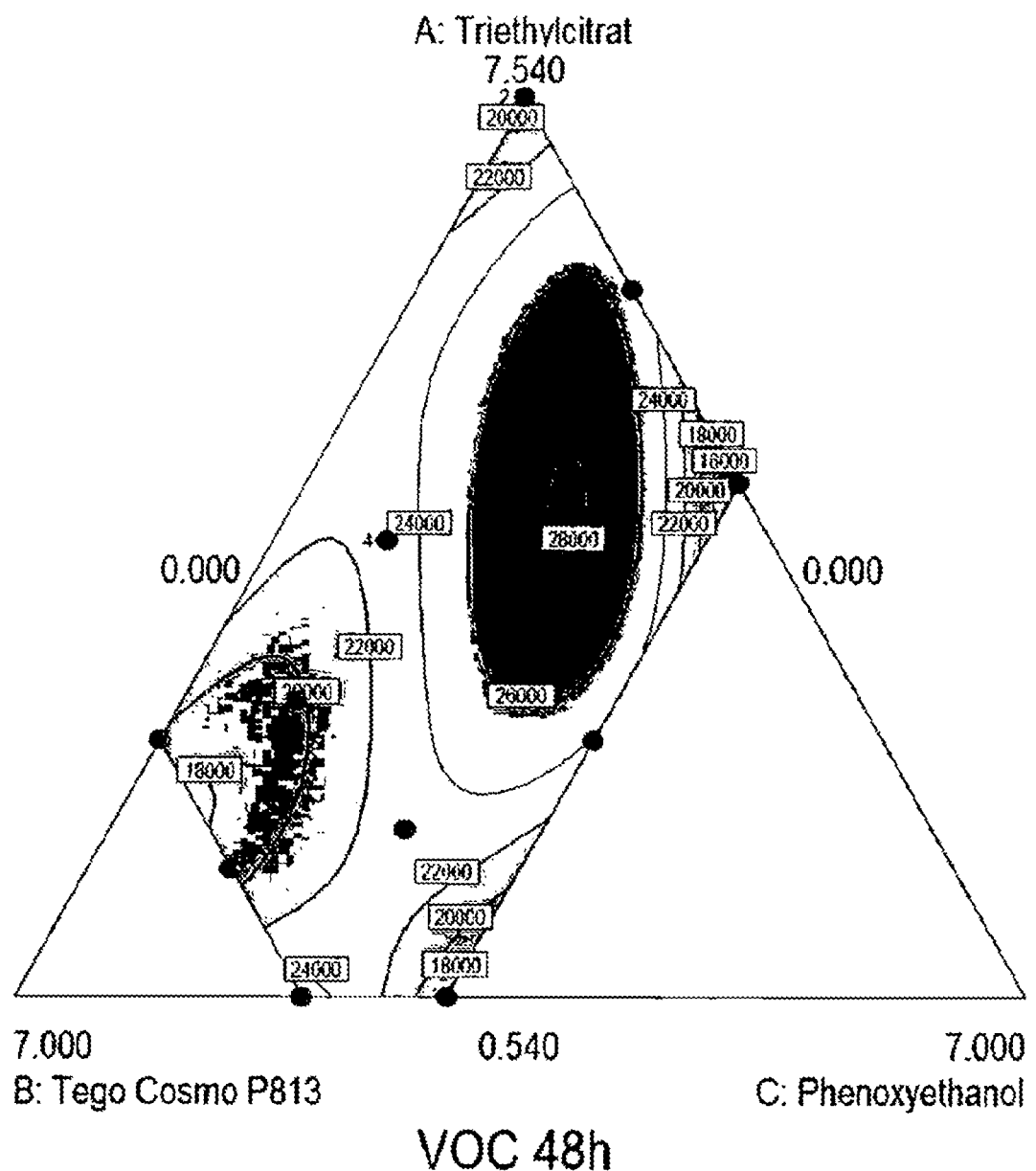

DEODORANTS WITH PROLONGED SCENT ADHESION

CROSS-REFERENCE TO RELATED APPLICATION

This application claims priority to German Patent Application No. 10 2017 217 735.7, filed Oct. 5, 2017, which is incorporated herein by reference in its entirety.

TECHNICAL FIELD

The present application relates to cosmetic and dermatological deodorant compositions which have improved and longer-lasting fragrance adhesion.

Moreover, the present disclosure relates to the cosmetic use of these compositions for the treatment of body odor.

BACKGROUND

Eccrine and apocrine sweat glands are present in the human armpit. While the eccrine glands produce aqueous secretions in response to heat, the apocrine glands secrete viscous secretions in response to stress. This apocrine sweat is a complex mixture that contains steroids, cholesterol and other fats and about 10% protein. Unpleasant body odor under the armpit develops from the initially odorless secretion through bacterial decomposition of the ingredients of the apocrine sweat.

The decomposition products of apocrine sweat, which contribute significantly to the body odor, in particular to the axillary body odor, can be divided into two classes: on the one hand into short-chain $C_4$-$C_{10}$ fatty acids, which may be linear, branched, saturated and unsaturated (for example, isovaleric acid), on the other hand into various steroid hormones and their metabolites (for example, 5-α-androstenol and 5-α-androstenone).

Body odor can be combated by avoiding the bacterial degradation of sweat or by using perfume to cover the body odor. In order to avoid the bacterial degradation of sweat, antimicrobials which reduce the number of sweat-decomposing bacteria on the skin by killing are used in the prior art. However, the effect of such antibacterial substances on the prevention of body odor and the use of perfume to cover the resulting body odor does not always result in a satisfactory deodorant performance.

The fragrance impression in the fight against body odor through the use of perfume is usually uncomfortably intense at the beginning. A high dosage of perfume oils is necessary, however, so that the perfume fragrance can be perceived on the skin as long as possible and covers the body odor. Nevertheless, the fixation of perfume fragrance (fragrance adhesion) often falls short of expectations. In addition, especially higher amounts of perfume oils may have a certain allergy potential. There is therefore still a need for cosmetic agents which have both a high and a long-lasting deodorizing effect against body odor.

BRIEF SUMMARY

The present disclosure has for its object to provide a cosmetic agent for reducing and/or preventing body odor, which agent has a good and long-lasting effect against body odor. In particular, these cosmetic agents should have an extended fragrance adhesion and a reduced risk of allergy.

It has now surprisingly been found that a mixture of aromatic alcohols, citric acid esters and polyglycerol fatty acid esters is outstandingly suitable as a fixing agent for fragrances in alcoholic and/or aqueous-alcoholic carriers, whereby not only an unexpectedly long deodorizing effect but also an optimal dosage of fragrances can be achieved.

A first subject matter of the present application is a cosmetic agent that contains (based on its total weight) from about 20 to about 98% by weight of at least one $C_1$-$C_4$ alcohol, from about 0.1 to about 10% by weight of at least one fragrance component, and at least one fixing agent for fragrance component b), including at least one aromatic alcohol, at least one citric acid ester and at least one polyglycerol fatty acid ester.

DESCRIPTION OF THE DRAWING

The Drawing is an illustration of a clear fragrance fixation after 48 hours of storing the sample in the warming cabinet.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The specification "% by weight" refers in the present case, unless otherwise stated, to the total weight of the cosmetic agents according to the present disclosure, wherein the sum of all ingredients of the agents according to the present disclosure yields about 100% by weight.

The cosmetic agent contains the constituents a) to c) for example in a cosmetically compatible carrier. Possible Exemplary cosmetically compatible carriers are alcoholic or aqueous-alcoholic media, wherein the aqueous-alcoholic media for example contain at least about 10% by weight of water, based on the total weight of the cosmetic agent. Alcoholic carriers are understood to mean media that contain essentially no free water.

"Substantially no" is understood to mean a free water content of not more than about 1% by weight, for example not more than about 0.5% by weight and in particular not more than about 0.1% by weight, based on the total weight of the cosmetic agent. Commercial products that contain water in minor amounts are not included in this.

Depending on the form of application, the compositions according to the present disclosure can be present both in an alcoholic carrier (and in this case up to about 98% by weight of alcohol, for example a $C_1$-$C_4$ alcohol) or in an aqueous-alcoholic carrier (and in addition to at least about 20% by weight of an alcohol, for example contain a $C_1$-$C_4$ alcohol, up to about 70% by weight of water). The cosmetically compatible carrier may for example be identical to component a).

Suitable alcohols are understood in particular to mean the lower alcohols customarily used for cosmetic purposes and having from about 1 to about 4 carbon atoms, for example ethanol and isopropanol.

Consideration is given in the cosmetic agents according to the present disclosure to ethanol as an alcoholic carrier or a mixture of ethanol and water (according to component a)).

A first possible embodiment is exemplified in that the cosmetic agents according to the present disclosure, based on their total weight, contain from about 22 to about 97% by weight, more for example from about 25 to about 95% by weight and in particular from about 27 to about 93% by weight of a $C_1$-$C_4$-alcohol, for example ethanol.

The cosmetic agents according to the present disclosure contain at least one fragrance component as a second constituent b). These are understood in principle to mean all cosmetically compatible perfumes, perfume oils or perfume oil constituents.

For the purposes of the present disclosure, perfume oils or fragrances can be individual fragrance compounds, for example, the synthetic products of the type of esters, ethers, aldehydes, ketones, alcohols and hydrocarbons. Fragrance compounds of the ester type are, for example, benzyl acetate, phenoxyethyl isobutyrate, p-tert-butylcyclohexyl acetate, linalyl acetate, dimethylbenzylcarbinylacetate (DMBCA), phenylethylacetate, benzylacetate, ethylmethylphenylglycinate, allylcyclohexylpropionate, styrallylpropionate, benzylsalicylate, cyclohexylsalicylate, floramate, melusate and jasmecyclate. The ethers include, for example, benzyl ethyl ether and ambroxane, aldehydes include, for example, the linear alkanals having from about 8 to about 18 carbon atoms, citral, citronellal, citronellyloxy-acetaldehyde, cyclamen aldehyde, lilial and bourgeonal, ketones include, for example, the ionones, alpha-isomethylionone, damascenone and methyl cedryl ketone, the alcohols include anethole, citronellol, eugenol, geraniol, linalool, phenylethyl alcohol and terpineol, the hydrocarbons include mainly the terpenes such as limonene and pinene. For example, however, mixtures of different fragrances are used, which together produce an attractive scent.

Such perfume oils may also contain natural fragrance mixtures such as those available from vegetable sources, for example, pine, citrus, jasmine, patchouli, rose or ylang-ylang oil. Also suitable are Muskateller sage oil, camomile oil, clove oil, lemon balm oil, mint oil, cinnamon leaf oil, lime blossom oil, juniper berry oil, vetiver oil, olibanum oil, *galbanum* oil and orange blossom oil, neroli oil, orange peel oil and sandalwood oil.

In order to be perceptible, a fragrance must be volatile, wherein the molecular mass also plays an important role in addition to the nature of the functional groups and the structure of the chemical compound. Thus, most fragrances have molecular masses up to about 200 daltons, while molar masses of about 300 daltons and above are more of an exception. Due to the different volatility of fragrances, the smell of a perfume or fragrance composed of several fragrances changes during evaporation, wherein the odor impressions are divided into top note, middle note or body, and base note, end note or dry out. Since odor perception is also largely based on the odor intensity, the top note of a perfume or fragrance does not consist solely of volatile compounds, while the base note consists for the most part of less volatile, i.e., adherent fragrances. In the subsequent classification of the fragrances as "more volatile" or "adherent" fragrances, nothing is stated about the odor impression and in addition, whether the corresponding fragrance is perceived as a top or middle note.

Adherent fragrances which can be used in the context of the present disclosure are, for example, the essential oils such as *angelica* root oil, aniseed oil, *arnica* blossom oil, basil oil, bay oil, bergamot oil, champaca blossom oil, silver fir oil, noble fir cone oil, elemi oil, *eucalyptus* oil, fennel oil, spruce alder oil, *galbanum* oil, geranium oil, gingergrass oil, Guaiac wood oil, gurdy balm oil, helichrysum oil, ho oil, ginger oil, iris oil, cajeput oil, calamus oil, chamomile oil, camphor oil, kanga oil, cardamom oil, *cassia* oil, pine needle oil, copaia balsam oil, coriander oil, spearmint oil, caraway oil, cumin oil, lavender oil, lemongrass oil, lime oil, tangerine oil, lemon balm oil, musk grain oil, myrrh oil, clove oil, neroli oil, niaouli oil, olibanum oil, orange oil, *origanum* oil, palmarosa oil, patchouly oil, peru balsam oil, petitgrain oil, pepper oil, peppermint oil, pimento oil, pine oil, rose oil, rosemary oil, sandalwood oil, celery oil, spik oil, star aniseed oil, turpentine oil, *thuja* oil, thyme oil, *verbena* oil, vetiver oil, juniper berry oil, wormwood oil, wintergreen oil, ylang-ylang oil, hyssop oil, cinnamon oil, cinnamon leaf oil, citronella oil, lemon oil and cypress oil.

However, the higher-boiling or fixed fragrances of natural or synthetic origin can also be used in the context of the present disclosure as odorous substances or odorous substance mixtures, i.e., fragrances. These compounds include the compounds listed below and mixtures thereof: Ambrettolide, alpha-amylcinnamaldehyde, anethole, anisaldehyde, anisalcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerate, borneol, bornyl acetate, alpha-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptincarboxylic acid methyl ester, heptaldehyde, hydroquinone dimethyl ether, hydroxycinnamaldehyde, hydroxycinnamyl alcohol, indole, iron, isoeugenol, isoeugenol methyl ether, isosafrole, jasmone, camphor, carvacrol, carvone, p-cresol methyl ether, coumarin, p-methoxyacetophenone, methyl n-amyl ketone, Methyl anthranilic acid methyl ester, p-methyl acetophenone, methyl chaviol, p-methyl quinoline, methyl beta naphthyl ketone, methyl n-nonyl acetaldehyde, methyl n-nonyl ketone, muscone, beta-naphthoethyl ether, beta-naphthol methyl ether, nerol, nitrobenzene, n-nonylaldehyde, nonyla alcohol, n-octylaldehyde, p-oxy-acetophenone, pentadecanolide, beta-phenylethyl alcohol, phenylacetaldehyde dimethyacetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, gamma-undelactone, vanillin, veratrum aldehyde, cinnamaldehyde, cinnamyl alcohol, cinnamic acid, cinnamic acid ethyl ester, cinnamic acid benzyl ester.

The more volatile fragrances include, in particular, the lower-boiling fragrances of natural or synthetic origin, which can be used alone or in mixtures. Examples of more volatile fragrances are alkyl isothiocyanates (alkyl mustard oils), butanedione, limonene, linalool, linayl acetate and propionate, menthol, menthone, methyl-n-heptenone, phellandrene, phenylacetaldehyde, terpinyl acetate, citral, citronellal.

For the purposes of the present disclosure, it has been found to be suitable when the fragrance component b) includes at least one compound, for example at least two compounds, from the group of limonene, lilial and damascenone. Fragrance components b) which contain at least one of the abovementioned compounds can be particularly well fixed on the application surface from an aqueous-alcoholic or alcoholic base with the fixing agent mixture c) and display a long-lasting effect there.

The aforementioned terms "limonene, lilial and damascenone" encompass both the individual enantiomers and racemic mixtures of these enantiomers. Alpha-damascone is suitable among the damascenons. These compounds have the following general structural formulas:

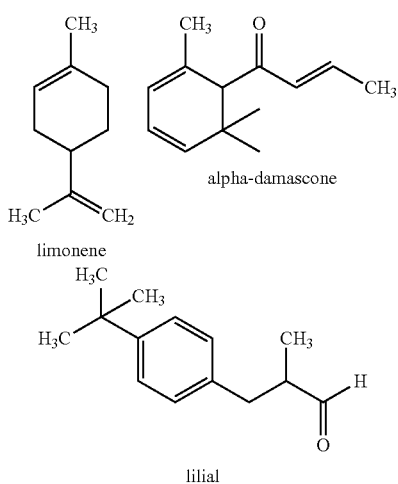

limonene alpha-damascone lilial

A second possible embodiment is exemplified in that the cosmetic agents according to the present disclosure contain at least one compound, for example at least two compounds, from the group of limonene, lilial and alpha-damascone as fragrance component b).

The at least one fragrance component b) is for example used in the compositions according to the present disclosure in an amount of from about 0.5 to about 10% by weight, more for example from about 0.75 to about 9% by weight and in particular from about 1 to about 8% by weight (based on the total weight of the cosmetic compositions). For example, the compositions according to the present disclosure contain at least one compound, for example at least two compounds, from the group of limonene, lilial and alpha-damascone in the abovementioned amounts as fragrance component b).

As a third constituent c), the cosmetic agents according to the present disclosure contain at least one fixing agent for the fragrance component(s) b), including at least one aromatic alcohol, at least one citric acid ester and at least one polyglycerol fatty acid ester.

Suitable aromatic alcohols are for example understood to mean 2-benzylheptan-1-ol, benzyl alcohol and/or phenoxyethanol, more for example benzyl alcohol and/or phenoxyethanol and in particular phenoxyethanol. These active ingredients, in conjunction with citric acid esters and polyglycerol fatty acid esters, are not only suitable as a fixing agent for fragrances but, as antibacterial agents, they simultaneously support bacterial degradation of sweat.

In a further possible embodiment, the cosmetic agents according to the present disclosure contain benzyl alcohol and/or phenoxyethanol, in particular phenoxyethanol, as an aromatic alcohol.

The at least one aromatic alcohol is for example used in the cosmetic compositions according to the present disclosure (based on their total weight) in amounts of from about 0.5 to about 3.5% by weight, more for example from about 0.75 to about 3.25% by weight from about 1 to about 3% by weight and in particular from about 1.4 to about 2.3% by weight.

Suitable citric acid esters are understood to mean mono-, di- or triesters of citric acid having at least one linear or branched, saturated or unsaturated alcohol having from about 1 to about 10, for example from about 1 to about 7 and especially having from about 1 to about 4, carbon atoms, wherein esters which are liquid under normal conditions have a boiling point >150° C., more for example >175° C. and for example >200° C., are possible. The methyl, ethyl and/or isopropyl esters of citric acid are suitable, and triethyl citrate is suitable.

In a possible embodiment, cosmetic agents according to the present disclosure include at least one mono-, di- or triester of citric acid and a linear or branched, saturated or unsaturated $C_2$-$C_{10}$ alcohol, for example triethyl citrate, as citric acid esters.

The at least one citric acid ester is for example used in the cosmetic compositions according to the present disclosure (based on their total weight) in amounts of from about 2 to about 7% by weight, more for example from about 2.5 to about 6.5% by weight, for example from about 3 to about 6% by weight and in particular from about 3.5 to about 5.5% by weight.

Suitable polyglycerol fatty acid esters are understood to mean compounds from the group polyglyceryl-6 behenates and/or polyglyceryl-2 caprate and/or polyglyceryl-3 caprate and/or potyglyceryl-4 caprate and/or polyglyceryl-5 caprate and/or polyglyceryl-6 caprate and/or polyglyceryl-10-caprate and/or polyglyceryl-2-caprylates and/or polyglyceryl-3-caprylates and/or polyglyceryl-4-caprylates and/or polyglyceryl-6-caprylates and/or polyglyceryl-10-caprylates and/or polyglyceryl-3-cetyl ethers and/or polyglyceryl-3 cocoate and/or polyglyceryl-4 cocoate and/or polyglyceryl-3 dicaprate and/or polyglyceryl-6 dicaprate and/or polyglyceryl-3 dicocoate and/or polyglyceryl-10 didecanoate and/or polyglyceryl-3-di-hydroxystearates and/or polyglyceryl-2 diisostearates and/or polyglyceryl-3 diisostearates and/or polyglyceryl-6 diisostearates and/or polyglyceryl-10 diisostearates and/or polyglyceryl-4 dilaurates and/or polyglyceryl-5 dilaurates and/or polyglyceryl-10-dilaurates and/or polyglyceryl dimer soyates and/or polyglyceryl-10 dimyristates and/or polyglyceryl-2 dioleates and/or polyglyceryl-3 dioleates and/or polyglyceryl-5 dioleates and/or polyglyceryl-6 dioleates and/or polyglyceryl-10 dioleates and/or polyglyceryl-6 dipalmitates and/or polyglyceryl-10 dipalmitates and/or polyglyceryl-2 dipolyhydroxystearates and/or polyglyceryl-2 distearates and/or polyglyceryl-3 distearates and/or polyglyceryl-6 distearates and/or polyglyceryl-10 distearates and/or polyglyceryl-2 isopalmitates and/or polyglyceryl-2 isostearates and/or polyglyceryl-3 isostearates and/or polyglyceryl-4 isostearates and/or polyglyceryl-5 isostearates and/or polyglyceryl-6 isostearates and/or polyglyceryl-10 isostearates and/or polyglyceryl-2 laurates and/or polyglyceryl-3 laurates and/or polyglyceryl-4 laurates and/or polyglyceryl-5 laurates and/or polyglyceryl-6 laurates and/or polyglyceryl-10 laurates and/or polyglyceryl-2 lauryl ethers and/or polyglyceryl-4 lauryl ethers and/or polyglyceryl-10 lauryl ether and/or polyglycerol-10 linoleates and/or polyglyceryl-2 myristates and/or polyglyceryl-3 myristates and/or polyglyceryl-5 myristates and/or polyglyceryl-6 myristates and/or polyglyceryl-10 myristates and/or polyglyceryl-2-oleates and/or polyglyceryl-3-oleates and/or polyglyceryl-4-oleates and/or polyglyceryl-5-oleates and/or polyglyceryl-6-oleates and/or polyglyceryl-8-oleates and/or Polyglyceryl-10 oleates and/or polyglyceryl-2 palmitates and/or polyglyceryl-3 palmitates and/or polyglyceryl-6 palmitates and/or polyglyceryl-10 palmitates and/or polyglyceryl-2 stearates and/or polyglyceryl-3 stearates and/or polyglyceryl-4 stearates and/or polyglyceryl-5 stearates and/or polyglyceryl-6 stearates and/or polyglyceryl-8 stearates and/or polyglyceryl-10 stearates.

Possible are the polyglyceryl caprates and caprylates such as polyglyceryl-2-caprates and/or polyglyceryl-3-caprates and/or polyglyceryl-4-caprates and/or polyglyceryl-5-caprates and/or polyglyceryl-6-caprates and/or polyglyceryl-10-caprates and/or polyglyceryl-2-caprylates and/or polyglyceryl-3-caprylates and/or polyglyceryl-4-caprylates and/or polyglyceryl-6-caprylates and/or polyglyceryl-10-caprylates.

Suitable is polyglyceryl-3-caprylates. Suitable polyglycerol fatty acid esters are commercially available, for example from the company Evonik (Tegosoft® PC31, Tegocare® PSC 3, Tego Cosmo® P 813) or by the company BASF (Lameform® TGI, Dehymuls® PGPH).

The at least one polyglycerol fatty acid ester is for example used in the cosmetic compositions according to the present disclosure (based on their total weight) in amounts of from about 0.1 to about 2.5% by weight, more for example from about 0.3 to about 2.25% by weight, for example from about 0.5 to about 2% by weight and in particular from about 0.7 to about 1.7% by weight.

In a suitable embodiment, the cosmetic compositions according to the present disclosure contain (based on their total weight)
from about 0.5 to about 3.5% by weight of at least one aromatic alcohol, for example benzyl alcohol and/or phenoxyethanol, from about 2.0 to about 7.0% by weight of at least one citric acid ester, for example triethyl citrate, and from about 0.1 to about 2.5% by weight of at least one polyglycerol fatty acid ester, for example polyglyceryl-2-caprylates and/or polyglyceryl-3-caprylates.

The adherence (fixing) of fragrances is usually adversely affected due to high alcohol contents and it has hitherto been necessary in predominantly alcoholic systems to continue to add higher amounts of emulsifiers and/or oils to the systems for the fixation of the fragrances for sufficient fragrance fixation (for at least about 48 hours).

This is not necessary in the compositions according to the present disclosure.

A further possible embodiment of the present disclosure is exemplified in that the cosmetic compositions contain substantially no further oil, wax and/or fatty substances in addition to the esters contained in the fixing agent c).

"Substantially none" in the context of the present disclosure means a content of not more than about 0.5% by weight, for example not more than about 0.25% by weight and in particular not more than about 0.10% by weight (based on the total weight of the cosmetic agents) of further oil, wax and/or fatty substances.

The cosmetic agents according to the present disclosure are for example deodorants, which may additionally contain antiperspirant compounds, such as, for example, aluminum and/or aluminum zirconium salts.

Cosmetic agents according to the present disclosure of a further possible embodiment are therefore exemplified in that they contain at least one antiperspirant compound, in particular antiperspirant aluminum and/or zirconium salts.

Antiperspirant compounds are understood to mean compounds according to the present disclosure which prevent or reduce perspiration of the sweat glands of the body. Furthermore, the terms "aluminum salt" and "aluminum zirconium salt" are understood to mean chemical compounds which are constructed of positively charged ions (also referred to as cations) in the form of zirconium and/or aluminum and negatively charged ions (also referred to as anions) in the form of halides, in particular chlorides, and hydroxides. There are ionic bonds between these ions.

In this connection, it is suitable when the cosmetic agents according to the present disclosure contain one of the following antiperspirant aluminum and/or zirconium salts and mixtures thereof:
(i) water-soluble astringent salts of aluminum, in particular aluminum chlorohydrate, aluminum sesquichlorohydrate, aluminum dichlorohydrate, aluminum hydroxide, potassium aluminum sulfate, aluminum bromohydrate, aluminum chloride, aluminum sulfate;
(ii) water-soluble astringent aluminum-zirconium salts, in particular aluminum zirconium-propylene glycol complexes, aluminum zirconium trichlorohydrex glycine, aluminum zirconium tetrachlorohydrex glycine, aluminum zirconium pentachlorohydrex glycine, aluminum zirconium octachlorohydrex glycine.

The compositions according to the present disclosure contain the antiperspirant compounds, in particular aluminum and/or zirconium salts, for example in amounts of from about 1 to about 30% by weight, for example in amounts of from about 2 to about 25% by weight, for example from about 3 to about 20% by weight, and in particular from about 4 to about 15% by weight (based on the total weight of the cosmetic compositions).

In the context of the present disclosure, it may be provided that the cosmetic agents according to the present disclosure contain further active ingredients and contents. These substances may in particular be selected from nonionic surfactants, chelating agents, thickening agents, deodorant active ingredients and mixtures thereof.

In the context of the present disclosure, it is advantageous when the cosmetic agents according to the present disclosure additionally contain at least one nonionic surfactant. The term "nonionic surfactants" is understood to mean compounds according to the present disclosure which contain at least one hydrophobic and at least one hydrophilic molecular part and no charged or ionizable groups. The hydrophobic radical is for example a hydrocarbon chain having from about 8 to about 28 carbon atoms, which may be saturated or unsaturated, linear or branched. This $C_8$-$C_{28}$ alkyl chain is for example linear. The hydrophilic molecular part is for example a poly(alkylene oxide), in particular poly(ethylene oxide) and/or poly(propylene oxide).

Cosmetic agents of the present disclosure which are possible according to the present disclosure are therefore exemplified in that they additionally contain a nonionic surfactant from the group of the polyalkylene glycol ethers, for example from the group of the alkoxylated $C_8$-$C_{24}$ alkanols having an average of from about 10 to about 100 moles of alkylene oxide per mole, for example from the group of ethoxylated $C_{12}$-$C_{18}$ alkanols having an average of from about 10 to about 30 moles of ethylene oxide per mole, the alkoxylated hydrogenated castor oils and mixtures thereof in a total amount of from about 0.1 to about 10% by weight, for example from about 0.2 to about 7.0 by weight, for example from about 0.3 to about 6.0% by weight, in particular from about 0.4 to about 5.0% by weight, based on the total weight of the cosmetic agent.

Suitable cosmetic agents of this embodiment contain nonionic surfactants from the group of hydrogenated castor oil having an average of about 40 moles of ethylene oxide, $C_{16}$-$C_{18}$ alcohols having an average of from about 2 to about 40 moles of ethylene oxide, in particular having an average of from about 10 to about 30 moles ethylene oxide, and mixtures thereof in the previously mentioned total quantities. The use of such surfactants allows a better incorporation of the ingredients and thus an improved storage stability of the cosmetic agents according to the present disclosure.

Furthermore, it may be possible in the context of the present disclosure when the cosmetic agents according to the present disclosure additionally contain at least one chelating agent. Chelating agents are understood to mean compounds according to the present disclosure which can bind to a central atom, in particular a metal atom, with at least two binding sites, in particular free electron pairs. It is therefore advantageous within the scope of the present disclosure when the cosmetic agent additionally contains at least one chelating agent selected from ethylenediaminetetraacetic acid (EDTA) and its salts, nitrilotriacetic acid (NTA) and its salts and mixtures thereof, in particular sodium salts of ethylenediaminetetraacetic acid (EDTA), in a total amount from about 0.01 to about 0.5% by weight, for example from about 0.02 to about 0.3% by weight, for example from about 0.03 to about 0.2% by weight, in particular from about 0.05 to about 0.1% by weight, based on the total weight of the cosmetic agent. Suitable cosmetic agents contain sodium salts of ethylenediaminetetraacetic acid (EDTA) in the total amounts given above. The deodorizing effect of the combination according to the present disclosure can be further increased through the use of such chelating agents. Furthermore, stabilization of the ingredients of the cosmetic agents and thus improved storage stability can be achieved.

The cosmetic agents according to the present disclosure are for example formulated as flowable preparations. The agents should be formulated in such a way that, on the one hand, they are easy to disperse, but on the other hand, they are sufficiently viscous that they remain at the site of action, in particular under the armpit, during the exposure time, and do not run or be excessively transferred to the clothing. Possible cosmetic agents are therefore exemplified in that they additionally contain at least one thickening agent selected from the group of cellulose ethers, xanthan gum, *sclerotium* gum, succinoglucans, guar gums, locust bean gum, nonionic hydroxyalkyl guar derivatives and locust bean gum derivatives, pectins, agar, carrageenan, tragacanth, gum arabic, karaya gum, tara gum, gellan, gelatin, casein, hydroxyalkylcelluloses, propylene glycol alginate, alginic acids and their salts, polyvinylpyrrolidones, polyvinyl alcohols, polyacrylamides, hydroxypropylated starch phosphates and octenyl starch succinates, acrylic acid acrylate copolymers, acrylic acid acrylamide copolymers, acrylic acid vinylpyrrolidone copolymers, acrylic acid vinylformamide copolymers and polyacrylates, in a total amount of from about 0.01 to about 2.0% by weight, in particular from about 0.1 to about 0.5% by weight, based on the total weight of the cosmetic agent. Possible thickening agents are selected from cellulose ethers, especially from hydroxyalkylcelluloses, in particular from hydroxypropylcellulose, hydroxypropylmethylcellulose, hydroxyethylcellulose, carboxymethylcellulose, cetylhydroxyethylcellulose, hydroxybutylmethylcellulose and methylhydroxyethylcellulose, and mixtures thereof. Hydroxyethyl cellulose is for example used as thickener.

Furthermore, it may be possible in the context of the present disclosure to use further deodorant active ingredients. Possible cosmetic agents according to the present disclosure are therefore exemplified in that they additionally contain at least one deodorant active ingredient in a total amount of from about 0.0001 to about 40% by weight, for example from about 0.2 to about 20% by weight, for example from about 1 to about 15% by weight, in particular from about 1.5 to about 5% by weight, based on the total weight of the cosmetic agent. If ethanol is used in the compositions according to the present disclosure, this does not apply as a deodorant active ingredient in the context of the present disclosure, but rather as a constituent of the carrier. Deodorant active ingredients possible according to the present disclosure are selected from the group of (i) silver salts; (ii) 1,2-alkanediols having from about 5 to about 12 carbon atoms, in particular 1,2-pentanediol, 1,2-hexanediol and 1,2-octanediol; (iii) active ingredients against exoesterases, in particular against arylsulfatase, lipase, beta-glucuronidase and cystathion-β-lyase; (iv) cationic phospholipids; (v) odor absorbers, in particular silicates, such as montmorillonite, kaolinite, ilit, beidellite, nontronite, saponite, hectorite, bentonite, smectite and talc, zeolites, zinc ricinoleate, cyclodextrins; (vi) deodorizing ion exchanger; (vii) antimicrobial agents; (viii) prebiotic active components; and (ix) mixtures of these deodorant active ingredients.

The cosmetic agents according to the present disclosure may be formulated as a propellant-driven aerosol. In this case, the agents contain at least one propellant.

Possible cosmetic agents according to the present disclosure are therefore exemplified in a further embodiment in that they contain at least one propellant.

Possible propellants (propellant gases) are propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, both individually and in combination. Hydrophilic propellant gases, such as carbon dioxide, can be used advantageously in the context of the present disclosure, when the proportion of hydrophilic gases is chosen low and lipophilic propellant gas (e.g., propane/butane) is present in excess. Suitable are propane, n-butane, isobutane and mixtures of these propellant gases. It has been found that the use of n-butane as the sole propellant gas can be suitable according to the present disclosure.

The total amount of the propellant is for example from about 5 to about 95% by weight, for example from about 20 to about 88% by weight. In particular from about 30 to about 80% by weight, each based on the total weight of the cosmetic agent including of the agent according to the present disclosure (=agent according to the present disclosure) and the propellant.

When vessels made of metal (aluminum, tinplate, tin), protected or non-splintering plastic or glass, which is coated with plastic outside, are considered as pressure gas containers, pressure and fracture resistance, corrosion resistance, easy fillability and aesthetic considerations, handiness, printability, etc. play a role in their selection. Special internal protective lacquers ensure the corrosion resistance with respect to the composition according to the present disclosure.

Suitable embodiments AF1 to AF67 of the cosmetic agents according to the present disclosure are listed in the following tables (all specifications in % by weight, unless stated otherwise). The embodiments AF1 to AF67 contain, in addition to citric acid ester(s) and polyglycerol fatty acid ester(s), no further oil, wax and/or fatty substances.

|  | AF1 | AF2 | AF3 | AF4 |
| --- | --- | --- | --- | --- |
| $C_1$-$C_4$ alcohol | 20-98 | 22-97 | 25-95 | 27-93 |
| Fragrance component | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |

-continued

|  | AF1 | AF2 | AF3 | AF4 |
|---|---|---|---|---|
| Water and, if necessary, other auxiliaries and additives | ad 100 | ad 100 | ad 100 | ad 100 |

|  | AF5 | AF6 | AF7 | AF8 |
|---|---|---|---|---|
| Ethanol | 20-98 | 22-97 | 25-95 | 27-93 |
| Fragrance component | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF9 | AF10 | AF11 | AF12 |
|---|---|---|---|---|
| $C_1$-$C_4$ alcohol | 20-98 | 22-97 | 25-95 | 27-93 |
| Limonene, lilial and/or alpha-damascone and possibly other fragrances | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF13 | AF14 | AF15 | AF16 |
|---|---|---|---|---|
| $C_1$-$C_4$ alcohol | 20-98 | 22-97 | 25-95 | 27-93 |
| Fragrance component | 0.10-10.00 | 0.50-10.00 | 0.75-9.00 | 1.00-8.00 |
| Phenoxyethanol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF17 | AF18 | AF19 | AF20 |
|---|---|---|---|---|
| $C_1$-$C_4$ alcohol | 20-98 | 22-97 | 25-95 | 27-93 |
| Fragrance component | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Triethylcitrate | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF21 | AF22 | AF23 | AF24 |
|---|---|---|---|---|
| $C_1$-$C_4$ alcohol | 20-98 | 22-97 | 25-95 | 27-93 |
| Fragrance component | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglyceryl-2-caprylates and/or polyglyceryl-3-caprylates | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF25 | AF26 | AF27 | AF28 |
|---|---|---|---|---|
| Ethanol | 20-98 | 22-97 | 25-95 | 27-93 |
| Limonene, lilial and/or alpha-damascone and possibly other fragrances | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF29 | AF30 | AF31 | AF32 |
|---|---|---|---|---|
| Ethanol | 20-98 | 22-97 | 25-95 | 27-93 |
| Fragrance component | 0.10-10.00 | 0.50-10.00 | 0.75-9.00 | 1.00-8.00 |
| Phenoxyethanol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF33 | AF24 | AF35 | AF36 |
|---|---|---|---|---|
| Ethanol | 20-98 | 22-97 | 25-95 | 27-93 |
| Fragrance component | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Triethylcitrate | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF37 | AF38 | AF39 | AF40 |
|---|---|---|---|---|
| Ethanol | 20-98 | 22-97 | 25-95 | 27-93 |
| Fragrance component | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |

-continued

|  | AF37 | AF38 | AF39 | AF40 |
|---|---|---|---|---|
| Polyglyceryl-2-caprylates and/or polyglyceryl-3-caprylates | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF41 | AF42 | AF43 | AF44 |
|---|---|---|---|---|
| Ethanol | 20-98 | 22-97 | 25-95 | 27-93 |
| Limonene, lilial and/or alpha-damascone and possibly other fragrances | 0.10-10.00 | 0.50-10.00 | 0.75-9.00 | 1.00-8.00 |
| Phenoxyethanol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF45 | AF46 | AF47 | AF48 |
|---|---|---|---|---|
| Ethanol | 20-98 | 22-97 | 25-95 | 27-93 |
| Limonene, lilial and/or alpha-damascone and possibly other fragrances | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Triethylcitrate | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF49 | AF50 | AF51 | AF52 |
|---|---|---|---|---|
| Ethanol | 20-98 | 22-97 | 25-95 | 27-93 |
| Limonene, lilial and/or alpha-damascone and possibly other fragrances | 0.10-10.00 | 0.50-10.00 | 0.75-9.00 | 1.00-8.00 |
| Aromatic alcohol | 0.50-3.50 | 0.75-3.25 | 1.00-3.00 | 1.40-2.30 |
| Citric acid ester | 2.00-7.00 | 2.50-6.50 | 3.00-6.00 | 3.50-5.50 |
| Polyglyceryl-2-caprylates and/or polyglyceryl-3-caprylates | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF53 | AF54 | AF55 | AF56 |
|---|---|---|---|---|
| Ethanol | 20-98 | 22-97 | 25-95 | 27-93 |
| Limonene, lilial and/or alpha-damascone and possibly other fragrances | 0.10-10.00 | 0.50-10.00 | 0.75-9.00 | 1.00-8.00 |
| Phenoxyethanol | 0.50-3.50 | 0.75-3.25 | 1.00-3.00 | 1.40-2.30 |
| Triethylcitrate | 2.00-7.00 | 2.50-6.50 | 3.00-6.00 | 3.50-5.50 |
| Polyglycerol fatty acid ester | 0.10-2.50 | 0.30-2.25 | 0.50-2.00 | 0.70-1.70 |
| Water and, if necessary, other auxiliaries and additives | ad 100 | ad 100 | ad 100 | ad 100 |

|  | AF57 | AF58 | AF59 | AF60 |
|---|---|---|---|---|
| Ethanol | 20-98 | 22-97 | 25-95 | 27-93 |
| Limonene, lilial and/or alpha-damascone and possibly other fragrances | 0.10-10.00 | 0.50-10.00 | 0.75-9.00 | 1.00-8.00 |
| Phenoxyethanol | 0.50-3.50 | 0.75-3.25 | 1.00-3.00 | 1.40-2.30 |
| Triethylcitrate | 2.00-7.00 | 2.50-6.50 | 3.00-6.00 | 3.50-5.50 |
| Polyglyceryl-2-caprylates and/or polyglyceryl-3-caprylates | 0.10-2.50 | 0.30-2.25 | 0.50-2.00 | 0.70-1.70 |
| Water and, if necessary, other auxiliaries and additives | ad 100 | ad 100 | ad 100 | ad 100 |

Deodorants, as Aerosol

|  | AF61 | AF62 | AF63 | AF64 |
|---|---|---|---|---|
| Triethylcitrate | 4.10 | 6.00 | 3.90 | 5.10 |
| Tego Cosmo ®[1] P 813 | 1.10 | 0.40 | 1.50 | 0.80 |
| Phenoxyethanol | 2.30 | 0.75 | 2.10 | 1.60 |
| Perfume, including limonene, lilial and/or alpha-damascone and possibly other fragrances | 4.00 | 4.00 | 4.00 | 4.00 |
| Ethanol | ad 100 | ad 100 | ad 100 | ad 100 |

The formulations AF1 to AF64 are in the weight ratio 1:4 filled with the propellant propane/butane (15/85) in aerosol cans.

Hydroalcoholic Solutions for Roll-on Application

|  | AF65 | AF66 | AF67 |
|---|---|---|---|
| Tylose ®[2] H | 0.40 | 0.40 | 0.40 |
| Eumulgin ®[3] B1 | 2.00 | 2.00 | 2.00 |
| Eumulgin ®[4] B2 | 2.00 | 2.00 | 2.00 |
| Ethanol | 30.0 | 30.0 | 40.0 |
| Locron ®[5] L | 16.0 | 16.0 | 16.0 |
| Perfume, including limonene, lilial and/or alpha-damascone and possibly other fragrances | 1.0 | 1.0 | 1.0 |
| Triethylcitrate | 3.50 | 4.00 | 4.30 |
| Tego Cosmo ®[1] P 813 | 1.70 | 0.60 | 1.00 |
| Phenoxyethanol | 2.10 | 1.00 | 2.20 |
| Water | ad 100 | ad 100 | ad 100 |

In the aforementioned embodiments AF61 to AF67, the following commercial products were used:
INCI name: POLYGLYCERYL-3 CAPRYLATE; Evonik
INCI name: HYDROXYETHYL CELLULOSE; Shin Etsu
INCI name: CETEARETH-12; BASF
INCI name: CETEARETH-20; BASF
INCI name: ALUMINUM CHLOROHYDRATE, AQUA; (AS 50%); Clariant A second subject matter of the present disclosure is the use of a cosmetic agent according to the present disclosure for the treatment of body odor.

A third subject matter of the present disclosure is the use of a mixture of at least one aromatic alcohol, at least one citric acid ester and at least one polyglycerol fatty acid ester for the fixation of fragrance components in an alcoholic or aqueous-alcoholic carrier.

With regard to further possible embodiments of the uses according to the present disclosure, in particular with regard to the cosmetic agents used, mutatis mutandis applies to the said cosmetic agents according to the present disclosure.

Effect Detection

The fixing agent mixture according to the present disclosure (2.00-7.00 triethyl citrate, 0.10-2.50 polyglyceryl-3-capryalates, 0.50-3.50 phenoxyethanol) was dissolved in ethanol with the fragrances limonene (1.33 by weight), lilial (1.33% by weight) and alpha-damascone (1.33% by weight). 30 μl of these mixtures were each applied to VITRO-Skin membranes, which were stored for about 48 h in a warming cabinet at about 30° C. The membranes were then transferred to an 8 l container and the volatile organic compounds in the gas compartment were quantified with the photoionization detector ppbRAE. The VOC values determined over a period of about 26 minutes are specified in ppb. The determined VOC values are attributable exclusively to the volatile fragrance components, since ethanol completely volatilizes under the experimental conditions (48 h at 30° C.).

A clear fragrance fixation after 48 hours of storing the sample in the warming cabinet can be seen in the Drawing. The experiment is based on a statistical experimental design and shows optimal results (>27000 ppb) for the fixing agent combination: 3.50-5.10 triethyl citrate; 0.40-1.70 polyglyceryl-3-capryalates; 0.75-2.30 phenoxyethanol While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent, comprising (based on its total weight)
   a) from about 20 to about 98% by weight of at least one $C_1$-$C_4$ alcohol,
   b) from about 0.1 to about 10% by weight of a fragrance component selected from the group consisting of limonene, lilial, alpha-damascone, and mixtures thereof, and
   c) a fixing agent for fragrance component b), comprising an aromatic alcohol selected from benzyl alcohol and phenoxyethanol;
   a citric acid ester; and
   a polyglycerol fatty acid ester or mixture of polyglycerol fatty acid esters.

2. The cosmetic agent according to claim 1, wherein it comprises (based on its total weight) from about 22 to about 97% by weight, of a $C_1$-$C_4$ alcohol.

3. The cosmetic agent according to claim 1, wherein the fragrance component comprises at least two compounds selected from limonene, lilial and alpha-damascone.

4. The cosmetic agent according to claim 1, comprising from about 0.50 to about 10% by weight of the fragrance component b).

5. The cosmetic agent according to claim 1, wherein it the aromatic alcohol comprises phenoxyethanol.

6. The cosmetic agent according to claim 1, wherein the citric acid ester comprises a mono-, di- or triester of citric acid and a linear or branched, saturated or unsaturated $C_2$-$C_{10}$ alcohol.

7. The cosmetic agent according to claim 1, wherein the polyglycerol fatty acid ester comprises, at least one of the compounds known under the INCI names Polyglyceryl Caprate and Polyglyceryl Caprylate.

8. The cosmetic agent according to claim 1, wherein it comprises substantially no further oil, wax and/or fatty substances in addition to the esters contained in the fixing agent c).

9. A composition comprising the cosmetic agent according to claim 1, and further comprising at least one propellant.

10. A composition comprising the cosmetic agent according to claim 1, and further comprising an antiperspirant compound.

11. The cosmetic agent according to claim 1, wherein the fixing agent comprises phenoxyethanol, triethylcitrate, and polyglyceryl caprate or polyglyceryl caprylate, and wherein the fixing agent comprises no further oil, wax, or fatty substances in addition to the esters in the fixing agent c).

12. A cosmetic agent, comprising (based on its total weight)
    a) from about 20 to about 98% by weight of a solvent comprising at least one $C_1$-$C_4$ alcohol,
    b) from about 0.1 to about 10% by weight of a fragrance component selected from the group consisting of limonene, lilial, alpha-damascone, and mixtures thereof, and
    c) a fixing agent for fragrance component b), comprising 0.5% to 3.5% by weight of an aromatic alcohol; 2.0% to 7.0% by weight of a citric acid ester; and 0.1% to 2.5% by weight of a polyglyceryl fatty acid ester or mixture of polyglycerol fatty acid esters.

13. The cosmetic agent according to claim 12, wherein the fixing agent c) comprises 0.75% to 2.3% by weight of the aromatic alcohol, 3.5% to 5.1% of the citric acid ester, and 0.4 to 1.7% by weight of the polyglyceryl fatty acid ester.

14. The cosmetic agent according to claim 12, wherein the citric acid ester comprises triethyl citrate.

15. The cosmetic agent according to claim 12, wherein the aromatic alcohol comprises phenoxyethanol.

16. The cosmetic agent according to claim 12, wherein the fixing agent comprises a polyglyceryl caprate or a polyglyceryl caprylate.

17. The cosmetic agent according to claim 16, wherein the fixing agent comprises a polyglyceryl-3-caprylate.

18. An antiperspirant composition comprising the cosmetic agent of claim 12 and further comprising an antiperspirant compound, wherein the antiperspirant compound comprises aluminum, zirconium, or both.

* * * * *